United States Patent [19]

Thompson

[11] 4,350,051

[45] Sep. 21, 1982

[54] INTERSTITIAL GAS PROBE

[76] Inventor: C. Keith Thompson, 11417 W. Ricks Cir., Dallas, Tex. 75230

[21] Appl. No.: 281,173

[22] Filed: Jul. 7, 1981

[51] Int. Cl.³ .............................................. G01N 1/22
[52] U.S. Cl. ................................. 73/864.74; 324/348
[58] Field of Search ...................... 73/864.74, 352, 73; 324/347, 348, 438

[56] References Cited

U.S. PATENT DOCUMENTS

| | | | |
|---|---|---|---|
| 1,901,431 | 3/1933 | Bond | 73/352 |
| 2,479,787 | 8/1949 | Stevens | 23/230 |
| 2,793,527 | 5/1957 | Turner et al. | 73/73 |
| 3,490,288 | 1/1970 | Patnode | 73/421.5 |
| 3,835,710 | 9/1974 | Pogorski | 73/421.5 R |
| 4,261,203 | 4/1981 | Snyder | 73/864.74 |
| 4,310,057 | 1/1982 | Brame | 73/864.74 |

FOREIGN PATENT DOCUMENTS

| | | | |
|---|---|---|---|
| 697606 | 11/1964 | United Kingdom | 324/438 |
| 1420747 | 1/1976 | United Kingdom | 73/864.74 |

Primary Examiner—S. Clement Swisher
Attorney, Agent, or Firm—Hubbard, Thurman, Turner, Tucker & Glaser

[57] ABSTRACT

A sample probe for obtaining relatively small subsurface gas samples for analysis during geo-chemical exploration. The probe is comprised of a long slender shaft capable of being driven into the soil and a hammer assembly which mounts to the shaft and is utilized to drive and remove the shaft. The shaft includes a passage for removal of interstitial gas and the passage may be mechanically sealed or opened while the probe is in place in the soil. The probe shaft also includes temperature, soil humidity and soil pH sensors which are utilized to obtain additional parameters to be considered during analysis of the gas samples.

18 Claims, 3 Drawing Figures

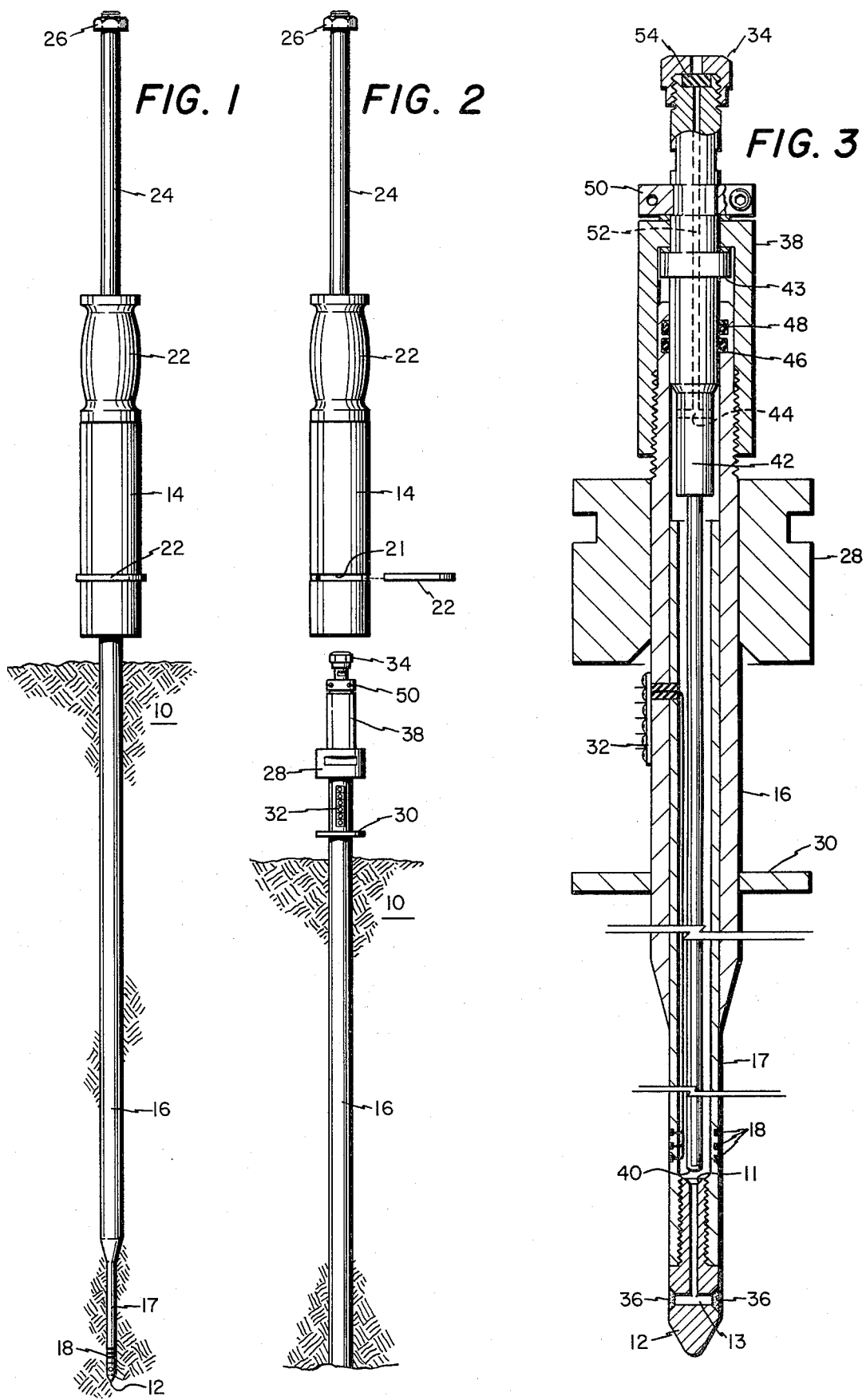

INTERSTITIAL GAS PROBE

BACKGROUND OF THE INVENTION

This invention relates to geochemical prospecting and exploration for subsurface deposits and more particularly to apparatus for detecting subsurface accumulations of hydrocarbon deposits, geothermal reservoirs, uranium or other mineral deposits by means of analysis of subsurface interstitial gas samples. Still more particularly, this invention relates to an apparatus for collecting gas samples and obtaining other important soil parameters which are useful in analysis of the gas samples.

Known subsurface gas sampling techniques are based upon the well known fact that geochemical and geophysical forces act upon subsurface accumulations of hydrocarbons or minerals and cause migration of many of the elements and compounds into the surrounding soil strata. Decomposition may take place during migration, resulting in primary and secondary constituents being partially or completely absorbed into surrounding soil or rock.

Typically, the concentration of such constituent elements is greatest at the surface above the source, and thus, analysis of concentration data concerning specific constituent elements can result in valuable information concerning the location of hydrocarbon deposits, geothermal reservoirs or mineral ore deposits. The development of concentration patterns is affected by many parameters, including: temperature, moisture, partial pressures, porosity of the soil strata and others.

Previously known apparatus for sampling subsurface gas have included simple mechanical probes and various bore hole techniques. One such example is depicted in U.S. Pat. No. 3,490,288, issued to H. W. Patnode. U.S. Pat. No. 3,490,288 is a mechanical probe which utilizes a rubber septum in the point to prevent contamination of the sampling passage, prior to sample selection. Such systems encountered great difficulty in preventing contamination, as the rubber septum at the point was often subject to damage during the driving of the probe into the soil.

An attempt to solve the problem encountered by contamination entering the sampling passage prior to sample selection is illustrated in U.S. Pat. No. 3,835,710, issued to L. A. Pogorski. U.S. Pat. No. 3,835,710 depicts a mechanical probe with a chisel shaped point assembly. The sample passage is a point at or near the threaded portion of the shaft which is received into the point assembly. At the appropriate sampling depth, the shaft is rotated to expose the sample passage. Difficulties have been encountered with this type of apparatus due to the chisel shaped point assembly rotating with the shaft.

SUMMARY OF THE INVENTION

It is therefore one object of the present invention to provide an improved subsurface gas sample probe.

It is another object of the present invention to provide a subsurface gas sample probe which may be easily inserted into and removed from the soil.

It is yet another object of the present invention to provide a subsurface gas sample probe which includes positive mechanical sealing of the sample passage prior to sampling.

It is another object of the present invention to provide a subsurface gas sample probe which includes temperature, soil moisture and soil pH measuring capability, at the sample depth.

The foregoing objects are achieved as is now described. The sample probe is comprised of a long slender shaft capable of being driven into the soil and a separate hammer assembly which may be mounted coaxially to the shaft and is utilized to drive and remove the shaft. The shaft includes a long narrow passage for removal of interstitial gas. The passage terminates at the probe tip and the probe tip includes a sealing surface. A sealing means within the passage may be mechanically actuated to engage the sealing surface and provide positive mechanical sealing of the sampling passage. The probe shaft also includes temperature, soil moisture and soil pH sensors which are utilized to obtain additional parameters to be considered during analysis of gas samples.

BRIEF DESCRIPTION OF THE DRAWINGS

The novel features believed characteristic of the invention are set forth in the appended claims. The invention itself; however, as well as a preferred mode of use, further objects and advantages thereof, will best be understood by reference to the following detailed description of an illustrative embodiment when read in conjunction with the accompanying drawings, wherein:

FIG. 1 depicts a diagramatic view of the subsurface soil gas sampling probe installed for use in accordance with the present invention;

FIG. 2 depicts a diagramatic view of the subsurface soil gas sample probe with the hammer assembly removed; and FIG. 3 depicts a cutaway sectional view of the shaft assembly of the subsurface gas sampling probe of the present invention.

DETAILED DESCRIPTION

Referring now to the figures and in particular to FIG. 1, there is depicted a region of soil 10, from which it is desired to remove a sample of gas. Probe tip 12 has been driven to a depth of several feet by means of probe driving assembly 14. The length of probe shaft 16 may vary, as a matter of design choice; however, experience has proven that subsurface gas samples taken from a depth of three or four feet are sufficient to identify areas of microseepage of hydrocarbon gases. Typically, sampled gases are subjected to hydrogen flame gas chromatography and analyzed for the lighter hydrocarbons, including methane, ethane, propane, isobutane, normal butane, isopentane and normal pentane, however, those ordinarily skilled in the art will appreciate that an interstitial sample probe of the type disclosed herein may be utilized to obtain samples of helium, oxygen or other gases found in soil strata.

Adjacent to probe tip 12 are sensing electrodes 18 which are utilized, in the illustrated embodiment, to sense soil temperature, soil moisture and soil pH. These and other parameters, when utilized in conjunction with the analysis of the sample gases, can result in an increased likelihood of accurate determination of locations of hydrocarbon or mineral ore deposits. While temperature, moisture and pH sensors are disclosed in the depicted embodiment, the sample probe of the present invention will accommodate a greater or lesser number of sensors, as dictated by the requirements of particular soil and environmental conditions.

Referring now to FIG. 2, there is depicted a diagramatic view of the gas sample probe of the present invention with probe driving assembly 14 removed, and the control mechanism of the probe exposed. Probe driving assembly 14 is designed to fit over the control mechanism and rest suspended on the upper surface of impact surface 28. Impact surface 28 is affixed to probe shaft 16 by any conventional method such as welding. Also affixed to probe shaft 16 is alignment disk 30. Alignment disk 30 serves to maintain the coaxial alignment of probe driving assembly 14 and probe shaft 16.

While probe driving assembly 14 is suspended from the upper surface of impact surface 28, key 20 is inserted into slot 21 of probe driving assembly 14 and serves to secure probe driving assembly 14 in place by locking against the lower surface of impact surface 28. Once locked in place, probe driving assembly 14 may be utilized to drive or remove the probe by operation of impact mass 22. Impact mass 22 is mounted to probe driving assembly 14 by means of shaft 24 and may be manually operated to repeatedly strike the upper surface of probe driving assembly 14 or the lower surface of restraining nut 26.

Also depicted in FIG. 2 is sensor terminal 32. Sensor terminal 32 is utilized to couple sensing electrodes 18 to appropriate measuring devices such as temperature measuring devices, pH meters or moisture level meters. The number of terminal contacts in sensor terminal 32 may be increased or decreased as a matter of design choice.

Referring now to FIG. 3, there is depicted a sectional view of the gas sample probe of the present invention. Probe tip 12 is constructed of a material which is sufficiently durable to allow easy penetration of various soil strata. Passage 13 is utilized to withdraw sample gases from the adjacent soil through filter elements 36. Filter elements 36 are constructed of any material sufficiently porous to allow gas to enter probe tip 12, without allowing particulate contamination to enter. In sample areas in which the soil is excessively moist, filter elements 36 may be constructed of a gas permeable membrane which will prevent the entry of moisture into the sample passage.

The longitudinal section of passage 13 is machined into a concave sealing surface 11, and the end of probe tip 12 is threaded into interior shaft 17. Running the entire length of interior shaft 17 is sealing rod 40. Sealing rod 40 is a solid rod which is machined into a spherical tip at one end and is fixedly mounted into control chamber 42 at the other end. The volume of gas present within interior shaft 17 during sampling may be varied by machining a flat surface on one side of sealing rod 40. Also present within interior shaft 17 are the electrical connections coupling sensing electrodes 18 to sensor terminal 32.

Control chamber 42 is constructed of a solid piece of metal which is machined into a taper at one end and is fixed to sealing rod 40 at the tapered end. Control chamber 42 is inserted into probe shaft 16 and forms a hermetic seal by means of O-rings 46 and 48.

Actuating nut 38 is threaded over control chamber 42 and onto probe shaft 16. As actuating nut 38 is tightened against raised ridge 43 on control chamber 42, sealing rod 40 is moved downward and engages sealing surface 11 with its spherical tip, effectively providing a mechanical seal which prevents gas from entering the sampling probe until desired.

A split collar 50 is attached to control chamber 42 above actuating nut 38 and as actuating nut 38 is unthreaded from probe shaft 16, control chamber 42 is raised, causing sealing rod 40 to raise, opening the sealed sampling passage.

Interstitial subsurface gasses from passage 13 are drawn upward through interior shaft 17 and into a transverse passageway 44 drilled through control chamber 42. A longitudinal pilot hole 52 is drilled through the axis of control chamber 42 and intersects transverse passageway 44. The top most end of control chamber 42 is threaded and machined to receive a rubber septum 54, which allows the upper end of the sampling passage to remain sealed until sampling. A cap 34 is utilized to protect septum 54.

During operation, sealing rod 40 is engaged with sealing surface 11 while the probe is driven into the soil. When the appropriate depth is achieved, a tool is utilized to engage the slots machined into impact surface 28 and another tool is utilized to unthread actuating nut 38. The sampling passages are thereby opened. A subsurface gas sample may be withdrawn through septum 54 by means of a common hypodermic syringe.

Although the invention has been described with reference to a specific embodiment, this description is not meant to be construed in a limiting sense. Various modifications of the disclosed embodiment, as well as alternative embodiments of the invention, will become apparent persons skilled in the art upon reference to the description of the invention. It is therefore contemplated that the appended claims will cover any such modifications or embodiments that fall within the true scope of the invention.

What is claimed is:

1. A probe for use in withdrawing subsurface soil gas samples, said probe comprising:
    an elongated shaft capable of being driven into the soil, said elongated shaft including a passage for removal of subsurface soil gas samples;
    a probe tip assembly, including a sealing surface, mounted at a first end of said passage;
    sealing means disposed within said passage; and
    actuating means at a second end of said passage for selectively enabling said sealing means to engage said sealing surface.

2. The probe according to claim 1 further including temperature sensing means disposed at said probe tip assembly and coupling means disposed at said second end of said elongated shaft for coupling said temperature sensing means to a measuring instrument.

3. The probe according to claim 1 further including a soil moisture sensing means disposed at said probe tip assembly and coupling means disposed at said second end of said elongated shaft for coupling said soil moisture sensing means to a measuring instrument.

4. The probe according to claim 1 further including a soil pH sensing means disposed at said probe tip assembly and coupling means disposed at said second end of said elongated shaft for coupling said soil pH sensing means to a measuring instrument.

5. A probe for use in withdrawing subsurface soil gas samples, said probe comprising:
    an elongated shaft capable of being driven into the soil, said elongated shaft including a passage for removal of subsurface gas samples;
    a probe tip assembly mounted at a first end of said passage, said probe tip assembly including a concave sealing surface disposed at the uppermost surface of said probe tip assembly;

an elongated sealing member disposed within said passage and having a substantially spherical surface at the lower end thereof; and actuating means disposed at the upper end of said elongated sealing member for selectively urging said substantially spherical surface into engagement with said concave sealing surface.

6. The probe according to claim 5 further including means coaxially mounted on said elongated shaft for driving said elongated shaft into the soil.

7. The probe according to claim 5 wherein said probe tip further includes filtration devices for filtering said subsurface soil gas samples.

8. The probe according to claim 5 wherein said actuating means comprises a threaded surface disposed on said elongated shaft and a mated threaded element affixed to said elongated sealing member whereby rotation of said threaded element will raise and lower said elongated sealing member.

9. The probe according to claim 5 further including temperature sensing means disposed at said probe tip assembly and coupling means disposed at said second end of said elongated shaft for coupling said temperature sensing means to a measuring instrument.

10. The probe according to claim 5 further including a soil moisture sensing means disposed at said probe tip assembly and coupling means disposed at said second end of said elongated shaft for coupling said soil moisture sensing means to a measuring instrument.

11. The probe according to claim 5 further including a soil pH sensing means disposed at said probe tip assembly and coupling means disposed at said second end of said elongated shaft for coupling said soil pH sensing means to a measuring instrument.

12. A probe for use in withdrawing subsurface soil gas samples, said probe comprising:

an elongated shaft capable of being driven into the soil, said elongated shaft including a passage for removal of subsurface gas samples;

a probe tip assembly mounted at a first end of said passage, said probe tip assembly including a substantially pointed penetrating member, a first gas passage disposed transversely above said substantially pointed penetrating member and a second gas passage connecting said first gas passage and a concave sealing surface disposed at the uppermost surface of said probe tip assembly;

an elongated sealing member disposed within said passage and having a substantially spherical surface at the lower end thereof; and actuating means disposed at the upper end of said elongated sealing member for selectively urging said substantially spherical surface into engagement with said concave sealing surface.

13. The probe according to claim 12 further including means coaxially mounted on said elongated shaft for driving said elongated shaft into the soil.

14. The probe according to claim 12 wherein said probe tip further includes filtration devices disposed in said first gas passage for filtering said subsurface soil gas samples.

15. The probe according to claim 12 wherein said actuating means comprises a threaded surface disposed on said elongated shaft and a mated threaded element affixed to said elongated sealing member whereby rotation of said threaded element will raise and lower said elongated sealing member.

16. The probe according to claim 12 further including temperature sensing means disposed at said probe tip assembly and coupling means disposed at said second end of said elongated shaft for coupling said temperature sensing means to a measuring instrument.

17. The probe according to claim 12 further including a soil moisture sensing means disposed at said probe tip assembly and coupling means disposed at said second end of said elongated shaft for coupling said soil moisture sensing means to a measuring instrument.

18. The probe according to claim 12 further including a soil pH sensing means disposed at said probe tip assembly and coupling means disposed at said second end of said elongated shaft for coupling said soil pH sensing means to a measuring instrument.

* * * * *